(12) United States Patent
Biedermann et al.

(10) Patent No.: US 10,022,158 B2
(45) Date of Patent: Jul. 17, 2018

(54) COUPLING ASSEMBLY FOR COUPLING A ROD TO A BONE ANCHORING ELEMENT, KIT OF SUCH A COUPLING ASSEMBLY DIFFERENT ROD RECEIVING ELEMENTS AND BONE ANCHORING DEVICE

(71) Applicant: Biedermann Technologies GmbH & Co. KG, Donaueschingen (DE)

(72) Inventors: Lutz Biedermann, VS-Villingen (DE); Wilfried Matthis, Weisweil (DE); Bernd Fischer, Braeunlingen (DE)

(73) Assignee: BIEDERMANN TECHNOLOGIES GMBH & CO. KG, Donaueschingen (DE)

( * ) Notice: Subject to any disclaimer, the term of this patent is extended or adjusted under 35 U.S.C. 154(b) by 0 days.

(21) Appl. No.: 15/229,740

(22) Filed: Aug. 5, 2016

(65) Prior Publication Data

US 2017/0027614 A1    Feb. 2, 2017

Related U.S. Application Data

(63) Continuation of application No. 14/339,304, filed on Jul. 23, 2014, now Pat. No. 9,439,680.
(Continued)

(30) Foreign Application Priority Data

Jul. 24, 2013 (EP) .................................... 13177919

(51) Int. Cl.
*A61B 17/70* (2006.01)
*A61B 17/56* (2006.01)
*A61B 17/68* (2006.01)

(52) U.S. Cl.
CPC ...... *A61B 17/7037* (2013.01); *A61B 17/7032* (2013.01); *A61B 17/7035* (2013.01); *A61B 2017/567* (2013.01); *A61B 2017/681* (2013.01)

(58) Field of Classification Search
CPC .................................... A61B 17/7035–17/704
See application file for complete search history.

(56) References Cited

U.S. PATENT DOCUMENTS

2007/0118123 A1    5/2007   Strausbaugh et al.
2008/0294202 A1    11/2008  Peterson
(Continued)

FOREIGN PATENT DOCUMENTS

JP    2008-539024 A    11/2008
JP    2013-500127 A    1/2013
(Continued)

OTHER PUBLICATIONS

Extended European Search Report for European Application No. 13177919.1, European Search Report dated Nov. 21, 2013 and dated Dec. 3, 2013 (7 pgs.).

*Primary Examiner* — Nicholas Plionis
(74) *Attorney, Agent, or Firm* — Lewis Roca Rothgerber Christie LLP

(57) ABSTRACT

A coupling assembly for coupling a rod to a bone anchoring element includes a receiving part having a recess for receiving the rod and an accommodation space with an opening for inserting and accommodating a head of the bone anchoring element, a pressure element having a first end surface and a flexible portion to clamp the head, and a rod receiving element configured to be assembled to the pressure element, the rod receiving element having a first end and a second end defining an opening, and a channel for receiving the rod. The channel has a bottom near the second end of the rod receiving element, and the opening of the rod receiving element opens into the channel. The first end surface of the pressure element can extend through the opening of the rod receiving element and past the bottom of the channel to contact the rod.

20 Claims, 12 Drawing Sheets

Related U.S. Application Data

(60) Provisional application No. 61/858,026, filed on Jul. 24, 2013.

(56) References Cited

U.S. PATENT DOCUMENTS

| | | |
|---|---|---|
| 2010/0160980 A1 | 6/2010 | Walsh et al. |
| 2012/0041490 A1 | 2/2012 | Jacob |
| 2012/0209336 A1 | 8/2012 | Jackson et al. |
| 2013/0018428 A1 | 1/2013 | Harper et al. |
| 2013/0060293 A1* | 3/2013 | Jackson ............ A61B 17/7037 606/305 |
| 2013/0072981 A1 | 3/2013 | Jackson et al. |
| 2013/0131734 A1* | 5/2013 | Longtain ............ A61B 17/7037 606/305 |
| 2014/0142634 A1* | 5/2014 | Schlaepfer ........... A61B 17/704 606/278 |

FOREIGN PATENT DOCUMENTS

| | | |
|---|---|---|
| JP | 2013-511326 A | 4/2013 |
| WO | WO 2006/116437 A2 | 11/2006 |
| WO | WO 2011/043805 A1 | 4/2011 |

\* cited by examiner

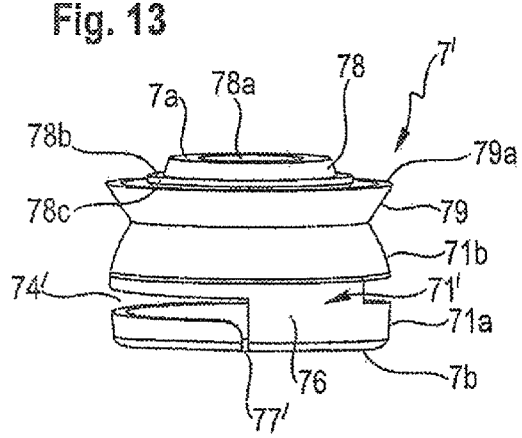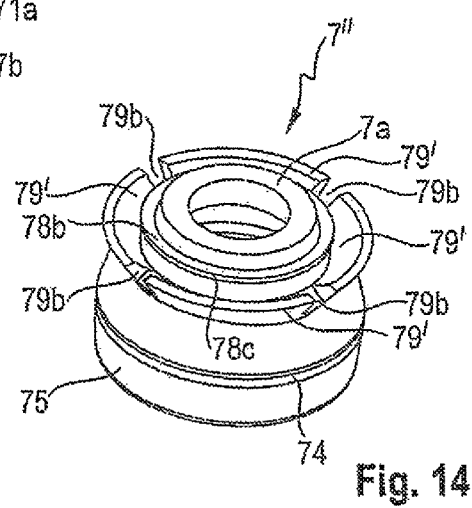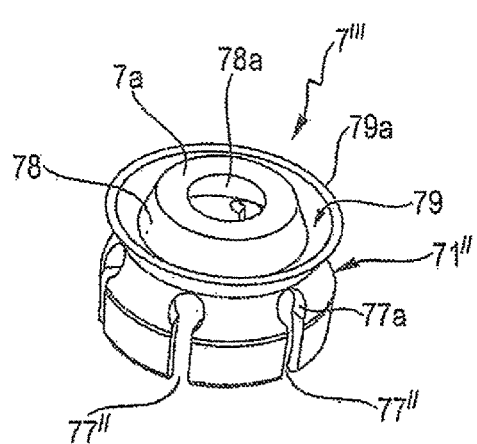

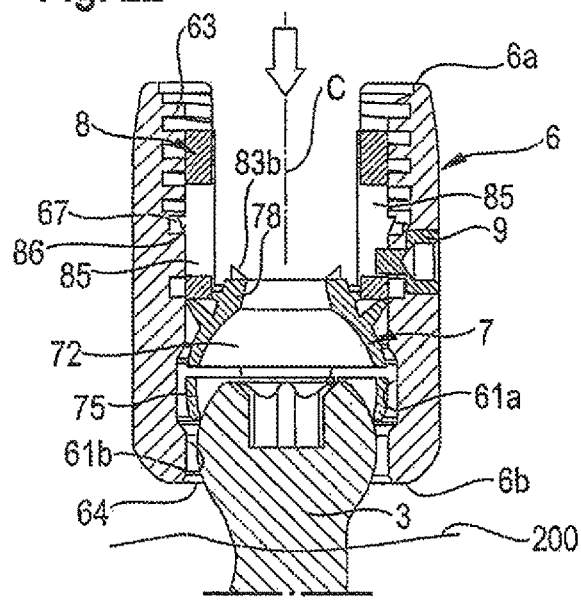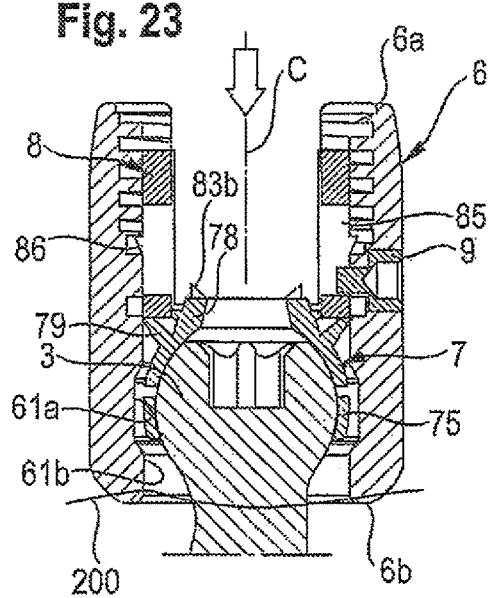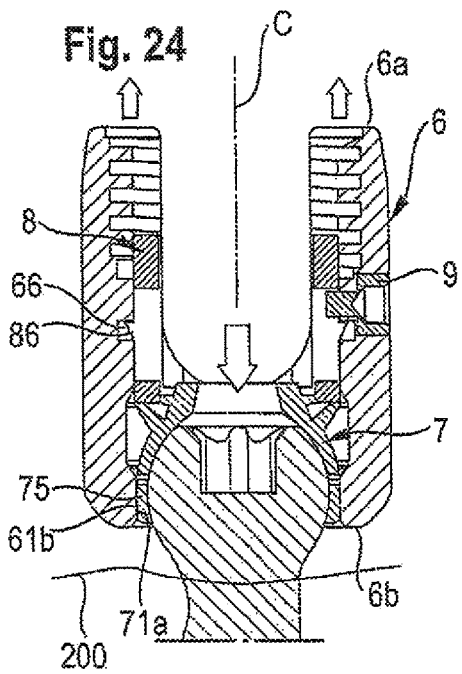

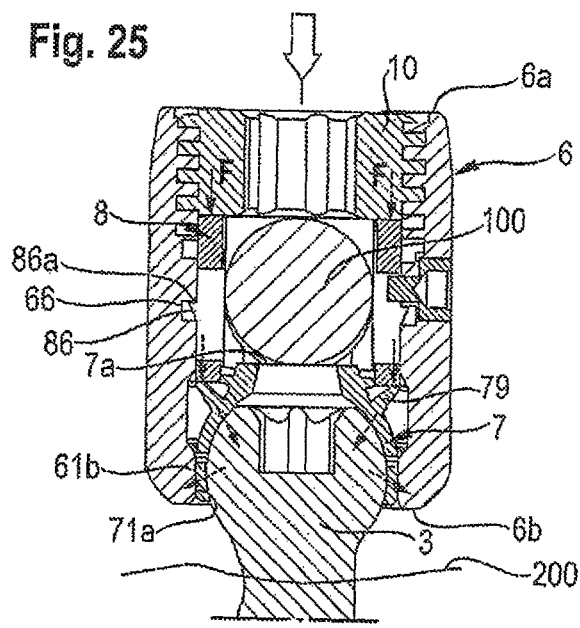
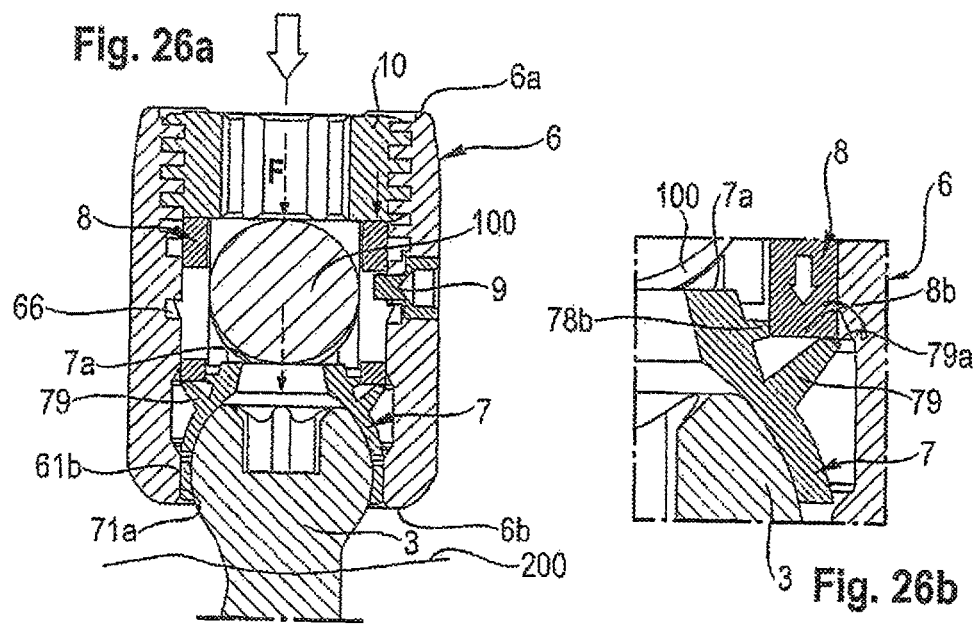

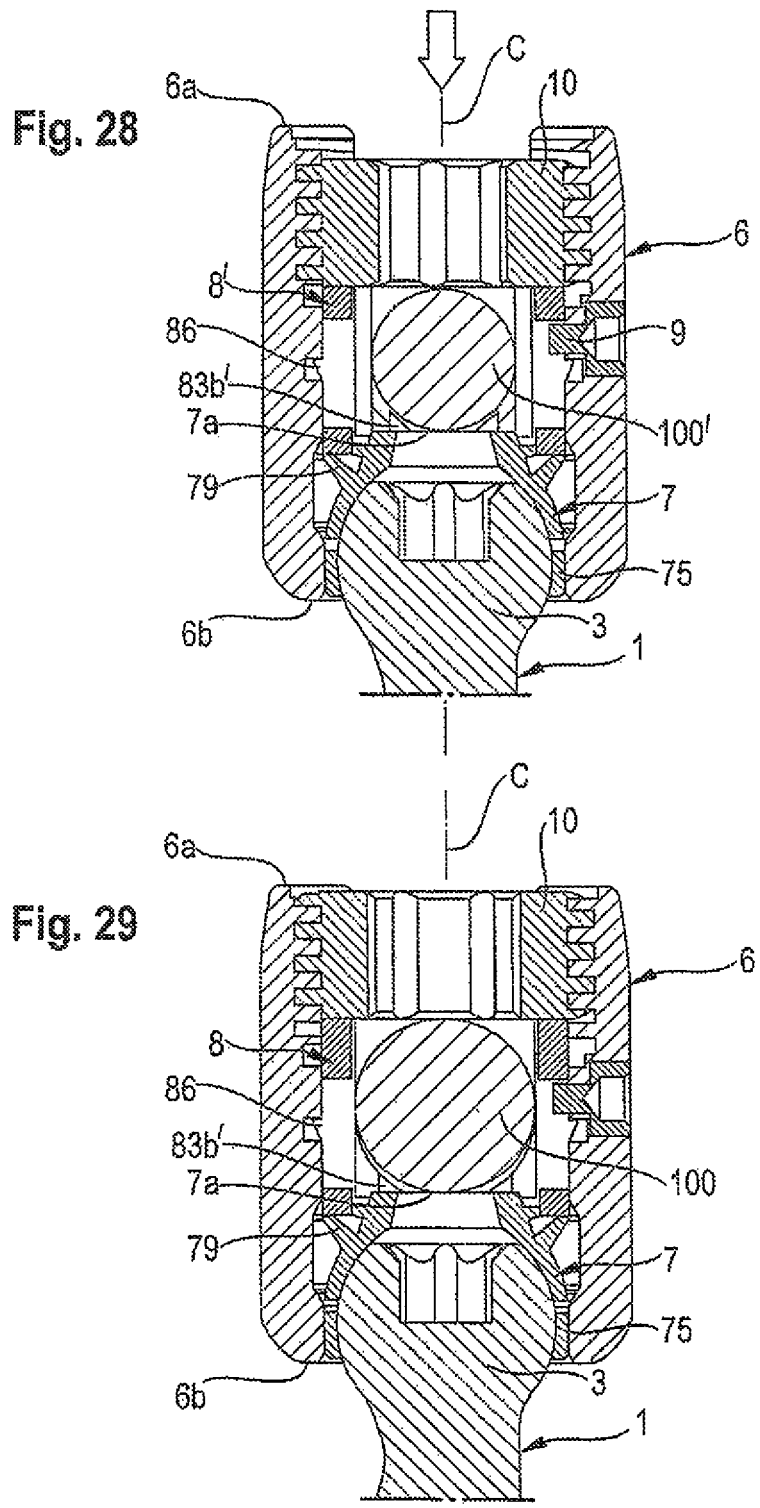

COUPLING ASSEMBLY FOR COUPLING A ROD TO A BONE ANCHORING ELEMENT, KIT OF SUCH A COUPLING ASSEMBLY DIFFERENT ROD RECEIVING ELEMENTS AND BONE ANCHORING DEVICE

CROSS-REFERENCE TO RELATED APPLICATION(S)

The present application is a continuation of U.S. patent application Ser. No. 14/339,304, filed Jul. 23, 2014, which claims priority to and the benefit of U.S. Provisional Patent Application Ser. No. 61/858,026, filed Jul. 24, 2013, the contents of which are hereby incorporated by reference in their entirety, and which claims priority from European Patent Application EP 13 177 919.1, filed Jul. 24, 2013, the contents of which are hereby incorporated by reference in their entirety.

BACKGROUND

Field

The invention relates to a coupling assembly for coupling a rod to a bone anchoring element, where the coupling assembly includes a receiving part with a recess for receiving the rod and an accommodation space for accommodating a head of the bone anchoring element. The coupling assembly further includes a pressure element to clamp the head and a rod receiving element that cooperates with the pressure element. The pressure element and the rod receiving element are configured to cooperate, such that when the anchoring element is inserted into the coupling assembly, the head of the bone anchoring element can be clamped first without fixing the rod, and subsequently the rod can be fixed using a single drive locking element. The invention further relates to a bone anchoring device including such a coupling assembly and a bone anchoring element. In addition, the invention relates to a kit including such a coupling assembly with different rod receiving elements to allow the use of rods with different diameters.

Description of Related Art

US 2010/0160980 A1 describes a locking mechanism and a method of fixation of a bone screw and a rod to the spine. The locking mechanism includes a body, an insert, a rod seat and a set screw. The body includes a bottom portion configured to receive the bone screw and the insert, but prevents the insert and the bone screw from passing therethrough once the insert and the bone screw are engaged. The rod seat is between the rod and the insert.

US 2013/0018428 A1 describes an orthopedic fixation device that includes a coupling element and a bone fastener, whereby the bone fastener can be loaded into the coupling element through the bottom of a bore in the coupling element.

SUMMARY

Embodiments of the invention provide a coupling assembly for coupling a rod to a bone anchoring element and a bottom loading polyaxial bone anchoring device that is improved regarding various aspects when compared with existing bone anchoring devices.

In particular, it is an object of the invention to provide an improved coupling assembly for coupling a rod to a bone anchoring element that provides improved or easier handling during surgery and that has an enlarged field of applications.

The coupling assembly has a structure that allows a sequential locking of the head of the bone anchoring element and the rod with a locking element using a single drive. By tightening the locking element, first the head is clamped relative to the coupling assembly while the rod is still movable. Upon deformation between cooperating portions of the pressure element and the rod receiving element, the rod can be fixed after locking of the head.

The pressure element may have a recess or a recessed portion at its inner wall that allows pivoting of the bone anchoring element to a larger angle in the direction of the recess or the inner recessed portion, compared to other directions. Because the pressure element is rotatable in the coupling element as long as the head is not locked, a position of the enlarged pivot angle can be selected for 360° around a central axis.

A rod receiving element engages with the receiving part in such a manner that the pressure element is held in a pre-locking position that prevents removal of the head of the bone anchoring element after the head is inserted. In the pre-locking position, the head of the bone anchoring element may be held by a frictional force exerted by the pressure element onto the head. The frictional force may be such that pivoting of the head relative to the coupling assembly is still possible by applying a force to overcome the frictional force.

According to an embodiment of the invention, the pressure element has a slit ring at its bottom end. The slit ring can expand in a radial direction to allow for insertion of the head of the bone anchoring element. The force necessary for introducing the head into such a flexible portion of the pressure element is reduced compared to pressure elements that have only longitudinal or coaxial slits. This further simplifies the handling during surgery.

The coupling assembly can be assembled in situ with a bone anchoring element that has been already inserted into a bone or a vertebra. The rod receiving element may be designed to receive a rod of a specific diameter or diameter range. By providing a kit including the coupling assembly with at least two rod receiving elements that are configured to receive rods of different diameters or diameter ranges, the coupling assembly can be used with rods of many different diameters. This enlarges the field of application of the bone anchoring device.

The bone anchoring device can be part of a modular system which includes, for example, several bone anchoring elements that may differ with respect to the lengths of the shanks, anchoring features of the shanks, such as different thread types, pitches, different diameters of the shanks, and cannulated or non-cannulated shanks. The modularity can further be increased by using the different rod receiving elements to couple the coupling assembly to rods of different diameters. This provides the surgeon with the choice between a large variety of implants. In addition, costs for stock-keeping may be reduced.

BRIEF DESCRIPTION OF THE DRAWINGS

Further features and advantages of the invention will become more apparent from the description of various embodiments using the accompanying drawings. In the drawings:

FIG. 13 shows a side view of a second embodiment of a pressure element;

FIG. 14 shows a perspective view from above of a third embodiment of a pressure element;

FIG. 15 shows a perspective view from above of a fourth embodiment of a pressure element;

FIG. 20b shows an enlarged portion of FIG. 20a;

FIG. 22 shows a cross-sectional view of a second step of assembling the bone anchoring device according to the first embodiment;

FIG. 23 shows a cross-sectional view of a third step of assembling the bone anchoring device according to the first embodiment;

FIG. 24 shows a cross-sectional view of a step of clamping a head of a bone anchoring element in the coupling assembly according to the first embodiment;

FIG. 25 shows a cross-sectional view of the bone anchoring device with an inserted rod and a locking element in a step of locking the head in the receiving part without locking the rod;

FIG. 26a shows a cross-sectional view of the bone anchoring device with the inserted rod and locking element in a step of locking the rod;

FIG. 26b shows an enlarged portion of FIG. 26a;

FIG. 28 shows a cross-sectional view of the bone anchoring device with an inserted rod of a first diameter and with a rod receiving element adapted to receive the rod of the first diameter;

FIG. 29 shows a cross-sectional view of the bone anchoring device with an inserted rod of a second diameter different than the first diameter and a locking element, and a rod receiving element adapted for use with the rod of the second diameter.

DETAILED DESCRIPTION

Figures 1, 2:
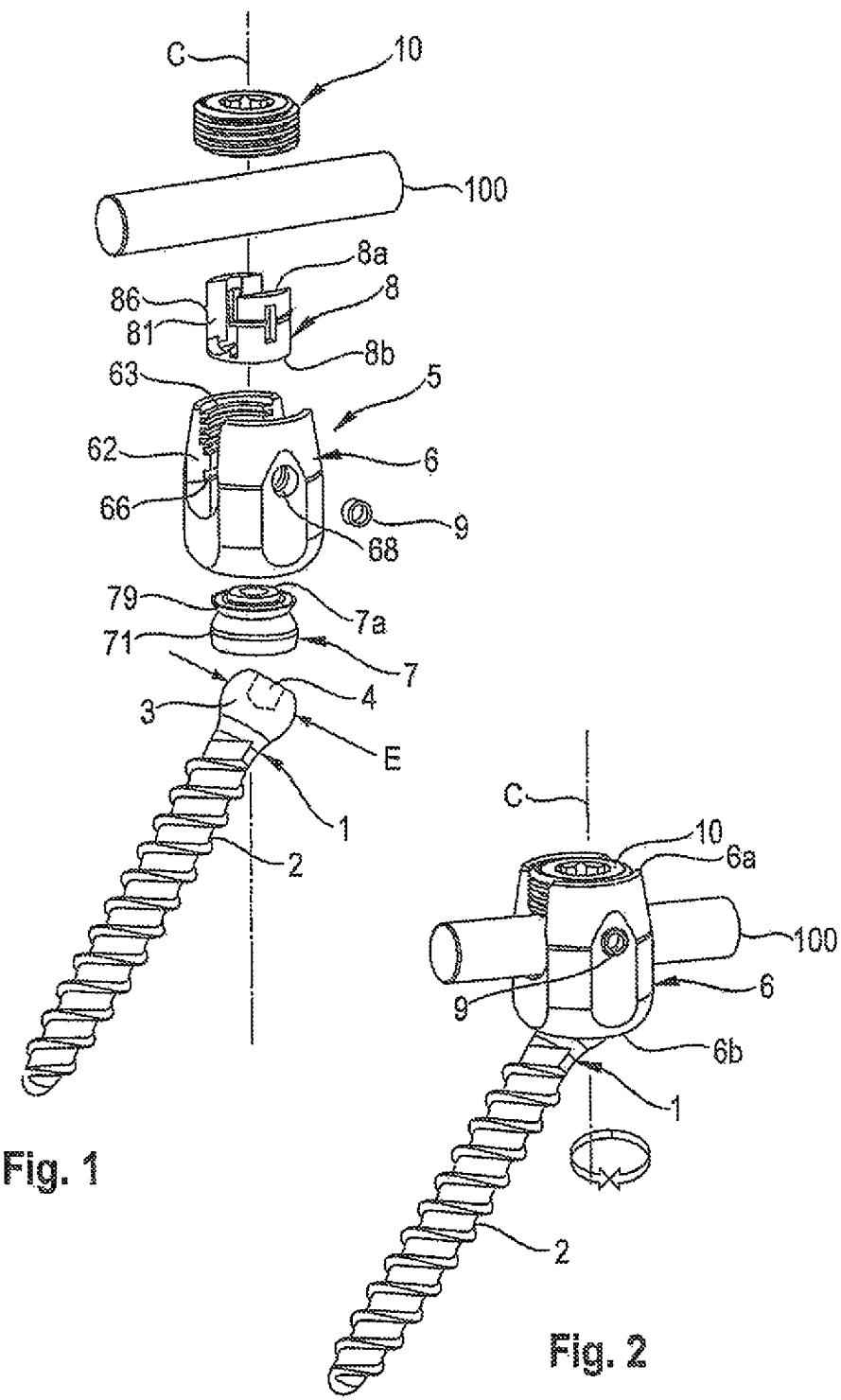
FIG. 1 shows an exploded perspective view of a first embodiment of a bone anchoring device.
FIG. 2 shows a perspective view of the bone anchoring device of FIG. 1 in an assembled state.

In FIGS. 1 and 2, a bone anchoring device according to a first embodiment includes a bone anchoring element 1 in the form of a bone screw having a shank 2 that is at least partially provided with a bone thread and a head 3. The head 3 has a spherical segment-shaped outer surface portion including a greatest outer diameter E of the sphere and a flat free end with a recess 4 for engagement with a screwing-in tool.

The bone anchoring device further includes a coupling assembly 5 for receiving a stabilization rod 100 and for coupling the stabilization rod 100 to the bone anchoring element 1. The coupling assembly 5 includes a receiving part 6 for receiving the head 3 of the bone anchoring element 1 and for receiving the rod 100, a pressure element 7 configured to be arranged in the receiving part 6, and a rod receiving element 8 also configured to be arranged in the receiving part 6. The pressure element 7 is utilized for locking the head 3 in the receiving part 6. The rod receiving element 8 is utilized for receiving the rod 100 and for acting on the pressure element 7 to lock the head 3. At least one pin 9 may also be provided for cooperating with the rod receiving element 8.

Further, a locking element 10 in the form of an inner screw is provided for securing the rod 100 in the receiving part 6 and the rod receiving element 8, and for exerting a force via the rod receiving element 8 onto the pressure element 7 to lock the head 3 in the receiving part 6.

The receiving part 6 will now be explained with reference to FIGS. 1 to 8. The receiving part 6 has a first end 6a that is a top end as illustrated and an opposite second end 6b that is a bottom end as illustrated, and a central axis of symmetry C passing through the first end 6a and the second end 6b. A bore 61 is provided that is coaxial to the central axis C. In a first region adjacent to the first end 6a, the receiving part 6 has as substantially U-shaped recess 62 with a bottom directed towards the second end 6b and two free lateral legs 62a, 62b extending towards the first end 6a. In the region of the legs 62a, 62b an internal thread 63 is provided that cooperates with the locking element 10. The channel formed by the U-shaped recess 62 is sized so as to receive the rod 100 therein, where the rod 100 is for connecting a plurality of bone anchoring devices. In the region of the legs 62a, 62b, from the first end 6a to substantially a height in the axial direction that is defined by the bottom of the U-shaped recess 62, the bore 61 has a first inner diameter. In a region below the legs 62a, 62b, towards the second end 6b, the bore 61 has a widened portion 61a with a diameter greater than the first inner diameter of the first portion. Between the second end 6b and the widened portion 61a, the bore 61 has a narrowing portion 61b that tapers towards the second end 6b with, for example, a cone angle. An opening 64 is provided at a second end 6b, where the diameter of the opening 64 is larger than the largest diameter E of the head 3, to allow for insertion of the head 3 from the second end 6b of the receiving part 6. The widened portion 61a and the narrowing portion 61b define an accommodation space for the head 3 of the bone anchoring element 1.

At a distance from the first end 6a below the internal thread 63, a circumferentially extending first groove 66 is provided at an inner surface of each of the legs 62a, 62b. The first groove 66 is utilized for engagement with a retaining portion of the rod receiving element 8, as further described below. A circumferentially extending second groove 67 may be provided at the lower end of the internal thread 63 that also serves for engagement with the retaining portion of the rod receiving element 8.

Figure 3:
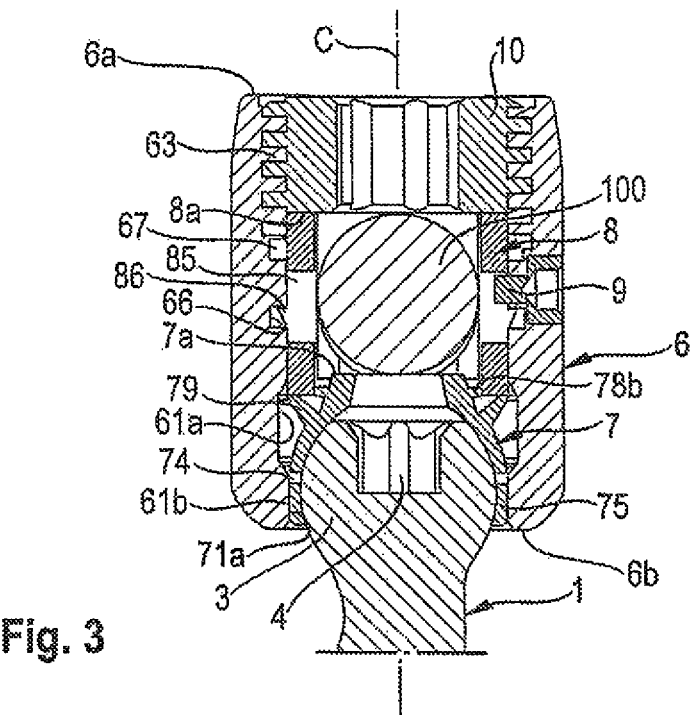
FIG. 3 shows a cross-sectional view of the bone anchoring device according to the first embodiment of FIGS. 1 and 2, the section taken perpendicular to an axis of an inserted rod.

On at least one of the legs 62a, 62b, a transverse bore 68 is provided that extends through the leg, for example through the leg 62b in the first embodiment, in a direction substantially perpendicular to the central axis C, for receiving the pin 9 (e.g., as seen in FIGS. 1-3). The bore 68 is located approximately at a center of the leg. The pin 9 preferably has such a length that once inserted into the bore 68, the pin 9 can extend a short distance into the bore 61 to provide a stop for the rod receiving element 8, as further described below. The pin 9 may be flush with the outer surface of the receiving part 6 when inserted.

As can be seen in particular in FIGS. 1 and 9 to 12, the pressure element 7 has a first end with a free end surface 7a, and a second end 7b. The second end 7b of the pressure element 7 is configured to be closer than the first end of the pressure element 7 to the second end 6b of the receiving part 6 when the pressure element 7 is arranged in the receiving part 6. Adjacent to the second end 7b the pressure element 7 has a cap-like flexible portion 71 that has a hollow interior chamber 72 that is substantially spherical segment-shaped. The cap-like portion 71 is open at the second end 7b, to allow the insertion of the head 3 of the bone anchoring element 1. An outer surface of the cap-like portion 71 has a narrowing portion 71a adjacent to the second end 7b that tapers and reduces in diameter towards the second end 7b. The taper corresponds substantially to a taper of the narrowing portion 61b of the receiving part 6. The narrowing portion 71a is adjacent to a substantially spherical segment-shaped outer surface portion 71b. At one circumferential position, there may be an internal recessed portion 73 adjacent to the second end 7b, so that the wall of the cap-like portion 71 is thinner at the recessed portion 73 than at other portions of the cap-like portion 71. A width and height of the recessed portion 73 is such that the shank 2 of the bone anchoring element can extend therein. This allows the shank 2 of the bone anchoring element 1 to be pivoted to a greater angle in the direction of the recessed portion 73 than in other directions when the head 3 of the bone anchoring element 1 is inserted in the pressure element 7. Hence, the pivot angle is enlarged to one side. The increased pivoting can be, for example, approximately 10° more than in other directions. However, other enlarged pivot angles may be contemplated and implemented, depending on the wall thickness and geometry of the recessed portion 73.

At a distance from the second end 7b, a circumferentially extending slit 74 is provided. The slit 74 extends circumferentially around the central axis C of the receiving part 7 along a plane substantially perpendicular to the central axis C when the pressure element 7 is arranged in the receiving part 6. Further, the slit 74 extends around more than 180°, and preferably more than 270°, and further preferably more than 340°, but not completely, around the central axis C. Therefore, by means of the slit 74, a ring-shaped portion 75 at the second end 7b is provided that is integrally connected to the rest of the pressure element 7 by a wall portion forming a connecting strip 76. The connecting strip 76 has such a length in the circumferential direction that it provides a stable connection of the ring-shaped portion 75 to the rest of the pressure element 7. At one end of the circumferentially extending slit 74, there is a substantially vertical slit 77 that extends from the second end fully through the ring-shaped portion 75 and into the slit 74. By means of this, the ring-shaped portion 75 is cut through or split in a circumferential direction and forms a slit ring 75 that can be expanded and compressed in a radial direction. A width of the vertical slit 77 is preferably smaller than the width of the circumferential slit 74. The outer surface of the slit ring 75 is tapered and forms the narrowing outer surface portion 71a towards the second end 76 of the pressure element 7. A position and size of the slit ring 75 is such that when the head 3 of the bone anchoring element 1 is inserted from the open end of the cap-like portion 71, the slit ring 75 expands so that the width of the vertical slit 77 becomes larger, and when the head 3 has been fully inserted into the hollow interior chamber 72, the slit ring 75 encompasses the head 3 at the largest diameter E and/or below the largest diameter E of the head 3 in a direction towards the shank 2.

A maximum outer diameter of the cap-like portion 71 is slightly smaller than the inner diameter of the first portion of the bore 61 of the receiving part 6, and is therefore also smaller than the diameter of the bore in the widened portion 61a. Hence, the slit ring 75 can expand in the widened portion 61a of the receiving part 6.

At the side of the cap-like portion 71 that is opposite to the second end 7b, a conically-tapered portion 78 is provided that tapers and narrows in diameter towards the first end surface 7a and that has a conical bore 78a that allows access to the recess 4 of the head 3 of the anchoring element 1. The conical portion 78 is of such a height and outer dimension that it can pass through a bottom opening of the rod receiving element 8 described below. At a distance from the first end surface 7a, an annular projection 78b is formed at the conical segment-shaped portion 78 that has, for example, a flat upper surface and an inclined lower surface. An outer circumferential surface 78c of the projection 78b may be substantially cylindrical.

At the transition between the cap-like portion 71 and the conical segment-shaped portion 78, there is a conically widening collar 79 that widens towards the first end surface 7a and that has a flat upper surface 79a forming an abutment for cooperating with a portion of the rod receiving element 8. The conical collar 79 extends outwards in a radial direction beyond the first end surface 7a and also beyond the projection 78b. The flat upper surface 79a is located in an axial direction below the first end surface 7a of the pressure element 7 (as illustrated). The structure and/or size of the collar 79 is such that the collar 79 is at least slightly deformable in an axial direction when, for example, an axial load acts upon the upper flat surface 79a. In this case, the collar 79 is spread outwards. The deformation of the collar 79 may be a resilient deformation.

FIG. 13 shows a modified embodiment of a pressure element. The pressure element 7' differs from the pressure element 7 only with respect to the transverse slit in the cap-like portion. The cap-like portion 71' has a slit 74' that extends from a substantially vertical slit 77' in a helix-shaped manner at least partially around the central axis. In a further modification, the slit 77' is not substantially vertical but is just a portion or extension of the helical slit 74'.

Another modified embodiment of the pressure element is shown in FIG. 14. The pressure element 7" differs from the pressure element 7 according to the embodiment shown in FIGS. 9 to 12 by the shape of the conical collar. The conical collar in this embodiment is interrupted at regular distances by slits 79b to form circumferential collar portions 79'. In the embodiment shown, four collar portions 79' are formed. With the number of slits 79b and the size and thickness of the collar portions 79', a specific flexibility of the collar region can be achieved.

A further modified embodiment of the pressure element is depicted in FIG. 15. The pressure element 7''' differs from the pressure element 7 shown in FIGS. 9 to 12 by the design of the cap-like portion. The cap-like portion 71" has a plurality of vertical slits 77" that are spaced equidistantly. The vertical slits 77" are open towards the second end 7b and have a widened circular portion 77a at an opposite end of the slits 77" located towards the first end of the pressure element 7'''. The number and size of the slits 77"—is selected to achieve a specific flexibility of the cap-like portion 71". Furthermore, the pressure element 7''' according to this embodiment does not have the annular projection 78b at the conical segment shaped portion 78.

It shall be understood that many different combinations of features of the various embodiments of the pressure elements discussed, and of other embodiments, can be combined to generate various other embodiments of the pressure element.

Referring now to FIG. 1 and FIGS. 16 to 19, the rod receiving element 8 is a part that is separate from the pressure element 7. Rod receiving element 8 is a substantially cylindrical part that has a first end with a free end surface 8a and an opposite second end with a free end surface 8b. Adjacent to the first end with the first end surface 8a, there is a substantially rectangular recess 81 that cuts out a portion of the cylinder such that two free upstanding legs 81a, 81b remain, where the free end surfaces of the legs 81a, 81b form the first end surface 8a. On the second end 8b, there is an opening 82, preferably a circular opening, that extends through the rod receiving element 8 into the recess 81. An inner diameter of the opening 82 is larger than an outer diameter of the first end surface 7a of the pressure element so that the first end surface 7a of the pressure element can extend through the opening 82 into the rod receiving element 8. Furthermore, the inner diameter of the opening 82 is substantially the same as or has a slight undersize compared to the outer diameter of the cylindrical outer surface portion 78c of the annular projection 78b provided at the conical segment-shaped portion 78 of the pressure element 7. Hence, the pressure element 7 can be held together with the rod receiving element 8 when the conical portion 78 extends through the opening 82 of the rod receiving element 8, and the cylindrical outer surface portion 78c of the projection 78 may contact the inner surrounding surface of the rod receiving element 8 at the opening 82 in an interference-fit manner.

On the bottom of the recess 81 between the legs 81a and 81b, two concave cylinder-segment shaped rod supporting projections 83a, 83b are respectively provided on both sides of the bore forming the opening 82. The radius of the concave portions 83a, 83b are preferably selected such that they are adapted to the radius of the specific rod to be used.

The rod supporting projections 83a, 83b may be separated from the legs 81a, 81b by a groove 84 on each side of the projections 83a, 83b. The width of the recess 81 is such that the rod 100 can be received in the recess 81. When the rod 100 is inserted into the recess 81 of the rod receiving element 8, rod 100 can rest on the rod supporting projections 83a, 83b. A height of the legs 81a, 81b is such that the first end surface 8a is located slightly above the upper rod surface (as illustrated) when the rod 100 is placed into the channel 81 and rests on the rod supporting projections 83a, 83b.

An outer diameter of the rod receiving element 8 is only slightly smaller than an inner diameter of the bore 61 of the receiving part 6, so that the rod receiving element 8 can move in the bore 61 and is guided therein.

The rod receiving element 8 further has at each leg 81a, 81b an elongate recess 85 that extends substantially from the bottom of the recess 81 to a distance from the first end surface 8a. The recesses 85 extend completely through each leg 81a, 81b in a radial direction. The recesses 85 have a width so that the pin 9 can be accommodated therein. A bottom end 85a of each elongate recess 85 forms a stop for the pin 9 when the pin 9 extends into the respective recess 85. The stop prevents the rod receiving element 8 from escaping through the first end 6a of the receiving part 6 when the pressure element 7 is in an inserting position. Furthermore, the recesses 85 may serve together with at least one pin 9 as a securing device to maintain the alignment between the recess 62 of the receiving part 6 and the recess or channel 81 of the rod receiving element 8.

Figure 20A:
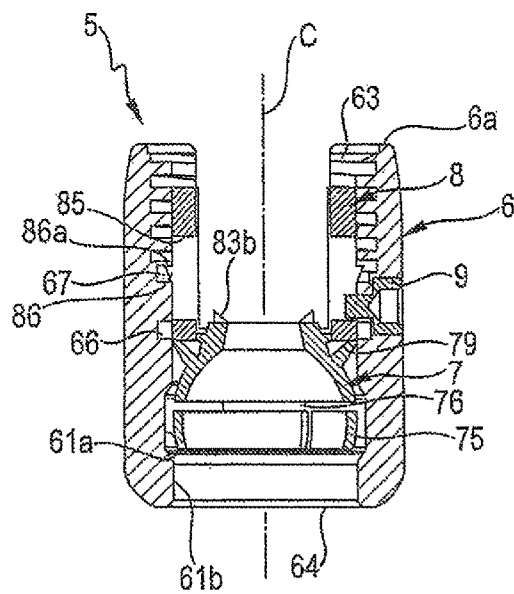
FIG. 20a shows a cross-sectional view of a coupling assembly of the bone anchoring device according to the first embodiment, where the pressure element and the rod receiving element are preassembled with the receiving part, and where the section is taken in a plane containing a central axis of the coupling assembly and that is perpendicular to an axis of an inserted rod.

The rod receiving element 8 also has on each leg 81a, 81b at approximately the center of each leg 81a, 81b in an axial direction, a circumferentially extending projection 86 with a flat upper surface 86a and an inclined lower surface 86b, the inclination of which is such that the projection 86 can more easily move out of the grooves 66, 67 when the rod receiving element 8 is pushed downwards towards the second end 6b of the receiving part 6. The shape of the projection 86 is such that, as can be seen in FIGS. 20a and 25, the projection 86 fits into the grooves 66, 67, respectively, and can abut with the upper flat surface 86a against the upper edges or surfaces of the grooves 66, 67.

Furthermore, on each leg 81a, 81b, a longitudinally extending cylinder segment-shaped recess 87 is provided that extends from the bottom of the recess 81 to the first end surface 8a.

The bone anchoring device, as a whole or in part, is made of a bio-compatible material, such as a bio-compatible metal or metal alloy, for example titanium, stainless steel, of a nickel-titanium alloy, for example, Nitinol, or of bio-compatible plastic materials, such as, for example, polyetheretherketone (PEEK).

Figure 20B:
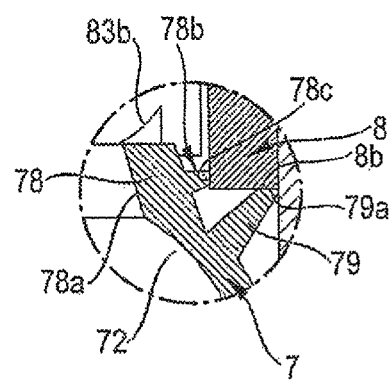

Referring to the embodiments in FIGS. 20a to 20c, the coupling assembly may be preassembled in the following manner. The rod receiving element 8 and the pressure element 7 are inserted into the receiving part 6. The pressure element 7 may be inserted through the lower opening 64 of the receiving part 6. The rod receiving element 8 may be inserted from the first end 6a of the receiving part by slightly pressing the legs 81a, 81b together until the projections 86 snap into the second groove 67. The pressure element 7 is in the first embodiment shown in FIGS. 20a and 20b temporarily held in the rod receiving element 8 by an interference fit. This is achieved by the cylindrical surface portion 78c of the projection 78b on the pressure element 7 that has a slight oversize with respect to the inner surface of the rod receiving element 8 at the opening 82. The rod receiving element 8 is prevented from escaping through the first end 6a of the receiving part 6 during insertion of the pressure element 7 because the flat upper surface 86*a* abuts against the upper edge of the second groove 67 in the receiving part 6. The pressure element 7 is also in its uppermost position, where the flat surface 79*a* of the collar 79 abuts against the second end surface 8*b* of the rod receiving element 8.

By means of this arrangement, the cap-like portion 71, and in particular the slit ring 75, is located at a position where the coaxial bore 61 has the widened portion 61*a* with the greatest inner diameter. As can be seen in FIG. 20*a*, the slit ring 75 has space to expand in this position.

Figure 20C:
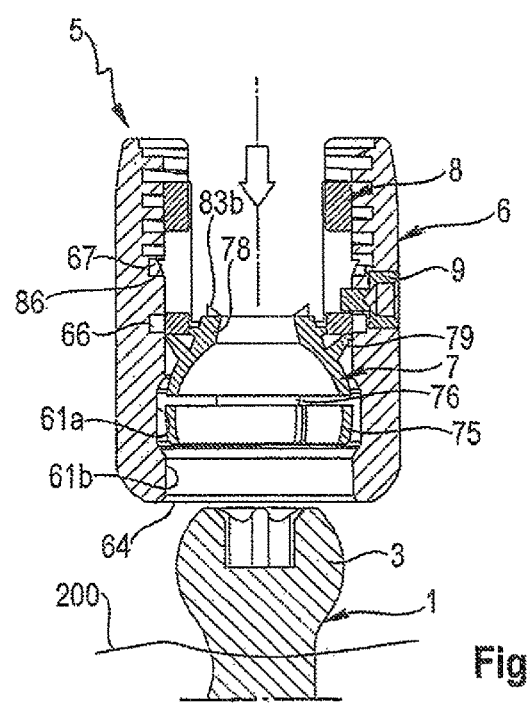
FIG. 20c shows an enlarged cross-sectional view of the cooperation between the receiving part, the pressure element and the rod receiving element in a modified example.

In an alternative embodiment, as shown in FIG. 20*c* in which the pressure element does not have the annular projection 78*b*, for example with the pressure element 7′″ as depicted in FIG. 15, the pressure element may not be held in the insertion position by an interference fit with the rod receiving element 8, but rather via a snap connection of the outermost edge of the collar 79 that may engage a third groove 69 at the inner surface of the receiving part 6. The third groove 69 may be small and shallow, as it is only necessary for holding the pressure element in the insertion position in such alternative embodiments.

Figure 21:
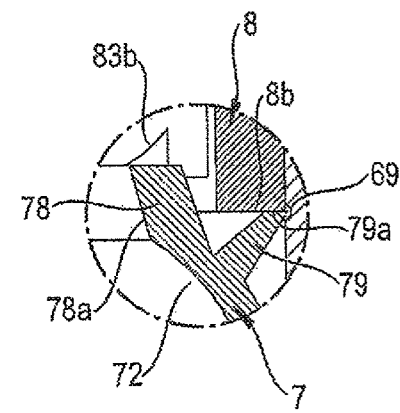
FIG. 21 shows a cross-sectional view of a first step of assembling the bone anchoring device according to the first embodiment.

Referring to FIGS. 21 to 26*b*, the use of the coupling assembly 5 together with a bone anchoring element 1 and a rod 100 will be explained. As depicted in FIG. 21, first, a suitable bone anchoring element 1 is implanted into the bone. In FIG. 21, the reference numeral 200 depicts the bone surface. Because the bone anchoring element 1 can be placed into the implantation site without the coupling assembly being connected thereto, the step of implanting the bone anchoring element 1 is more easily facilitated. Thereafter, the coupling assembly 5, with the pressure element 7 and the rod receiving element 8 in the insertion position relative to the receiving part 6, is placed onto the head 3 of the bone anchoring element 1. As depicted in FIGS. 22 to 23, the head 3 enters the receiving part 6 through the lower opening 64 and enters the cap-like portion 71 of the pressure element 7 through the open second end 7*b* of the pressure element 7. When the head 3 touches the slit ring 75 of the pressure element 7, the pressure element 7 presses with the collar 79 against the second end surface 8*b* of the rod receiving element 8 and shifts the rod receiving element 8 upward until the bottom 85*a* of the elongate recess 85 of the leg 81*b* abuts against the pin 9 extending through the leg 62*b* of the receiving part 6. Hence, the rod receiving element 8 is prevented from being pushed out through the first end 6*a* of the receiving part 6 when the head 3 is inserted.

The pressure element 7 is rotatable in the receiving part 6. The pressure element 7 may be placed such that the recessed portion 73 that provides the enlarged pivot angle is at a specific or desired position. To achieve this, an alignment feature (not shown) can further be provided that allows rotation of the pressure element 7 to arrange the recessed portion 73 in a desired position relative to the receiving part 6.

Further introduction of the head 3 into the cap-like portion 71 expands the slit ring 75 within the widened portion 61*a* of the bore 61 of the receiving part 6. The head 3 can then be completely inserted. Because the slit ring 75 does not expand at the connection strip 76, the insertion of the head 3 may not be precisely coaxial with the central axis C, but instead may occur slightly out of line or misaligned with the central axis C. By the further introduction of the head 3, the slit ring 75 may be expanded to a maximum extent, and may allow the head 3 to enter the upper portion of the hollow interior chamber 72 until the head 3 abuts against the inner wall of the chamber 72. Here, the slit ring 75 can elastically contract around the head 3, as shown in FIG. 23.

When the head 3 abuts against the inner wall of the cap-like portion 71 in the upper region, the slit ring 75 encompasses a portion of the head 3 below the region with the largest diameter E as can be seen in FIG. 23. In this condition, the slit ring 75 frictionally clamps the head 3, so that the bone anchoring element 1 can be pivoted to a desired angular position relative to the receiving part 6, and can be held there by the friction fit between the pressure element 7 and the head 3.

Finally, pulling the receiving part 6 in a direction away from the bone anchoring element 1 and/or pressing down the rod receiving element 8 in the opposite direction, as depicted by the arrows illustrated in FIG. 24, for example, with an instrument (not shown), presses the slit ring 75 into the narrowing portion 61*b*, so that the tapered outer surface 71*a* of the slit ring 75 engages the narrowing portion 61*b* of the receiving part 6. Simultaneously, the projection 86 snaps into the first groove 66 of the receiving part 6. In this condition, as depicted in FIG. 24, the rod receiving element 8 is prevented from moving upward because of the stop provided by the upper edge of the groove 66 against which the flat upper surface 86*a* of the projection 86 of the rod receiving element 8 abuts. The head 3 is already clamped by the cap-like portion 71 of the pressure element 7. Because the slit ring 75 is located between the head 3 and the narrowing portion 61*b* of the receiving part 6, the slit ring 75 can no longer expand in this position, and the head 3 is prevented from falling out or being pushed out through the lower opening 64. This is a pre-locking condition.

In clinical use, usually at least two bone anchoring devices are inserted into the bone and the receiving parts 6 are aligned. Because the heads 3 of the bone anchoring elements 1 are held in the pressure elements 7 by a frictional force, the receiving parts 6 can be easily aligned manually and their angular positions are maintained by the frictional forces between the heads 3 and the pressure elements 7. Then, as can be seen in FIG. 25, the rod 100 is inserted into the receiving part 6 of each device and the locking element 10 is screwed between the legs 62*a*, 62*b* of the receiving part 6. The rod 100 first is supported by the support surfaces 83*a*, 83*b* of the rod receiving element 8. Tightening of the locking element 10 moves the rod receiving element 8 slightly downward while the locking element 10 only contacts the first end surface 8*a* of the rod receiving element 8 and exerts a force on the first end surface 8*a*. The force F is transferred via the second end surface 8*b* of the rod receiving element 8 onto the upper flat end surface 79*a* of the collar 79 of the pressure element 7, onto the head 3, and from the head 3 onto the slit ring 75 and the receiving part 6, as depicted in FIG. 25. By means of this, the head 3 is locked in its angular position with respect to the receiving part 6 while the rod 100 is still movable relative to the receiving part 6 in the direction of the rod axis.

Referring now to FIG. 26*a* and FIG. 26*b*, a further advancement of the locking element 10 results in the second end surface 8*b* exerting a larger force F onto the upper surface 79*a* of the collar 79 of the pressure element 7 so that the collar 79 is slightly deformed, as can be seen more clearly in FIG. 26*b*. By means of this, the rod receiving element 8 can move slightly further downwards in the receiving part 6 and relative to the pressure element 7 and the rod 100, so that the locking element 10 presses onto the rod 100. Thereby, the rod 100 is also fixed. In this condition, the rod 100 may come into contact with the pressure element 7, so that the force is transmitted through the rod 100 and the first end surface 7a of the pressure element 7 onto the head 3 and the receiving part 6.

Figure 4:
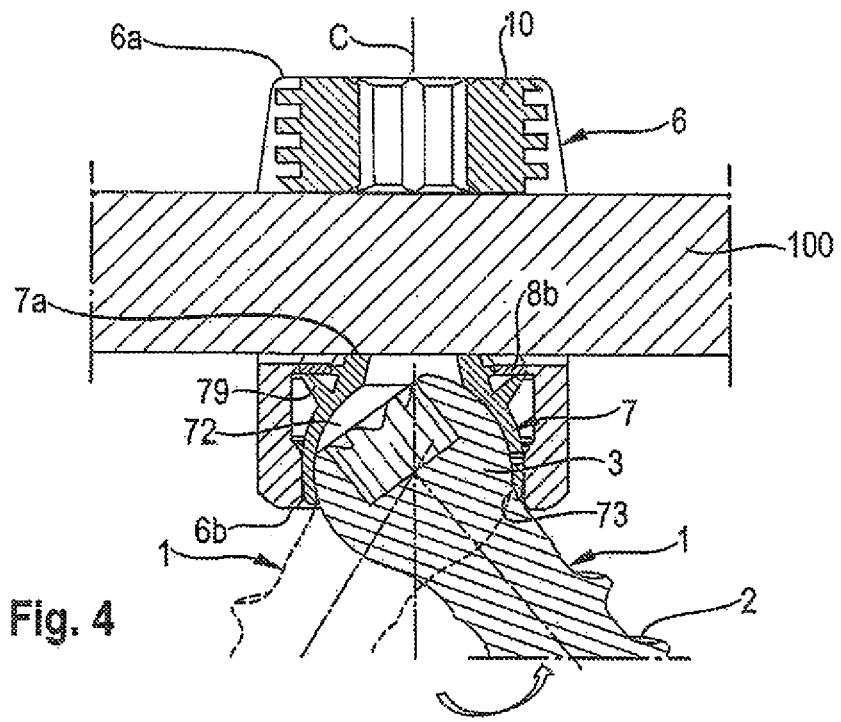
FIG. 4 shows a cross-sectional view of the bone anchoring device according to the first embodiment of FIGS. 1 and 2, the section taken in a plane containing a central axis of the device and a rod axis of an inserted rod.
Figure 5:
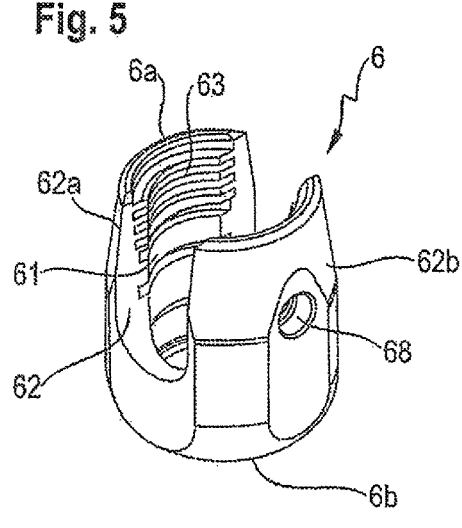
FIG. 5 shows a perspective view from above of a receiving part according to the first embodiment.
Figure 6:
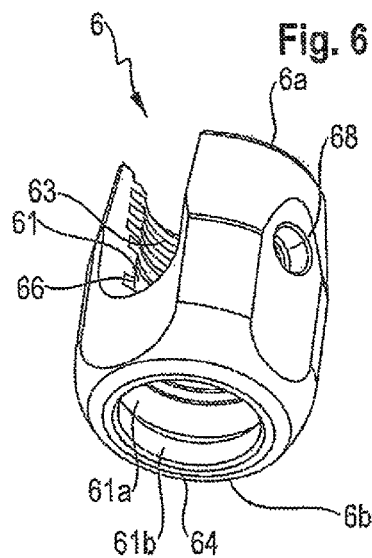
FIG. 6 shows a perspective view from the bottom of the receiving part shown in FIG. 5.
Figure 7:
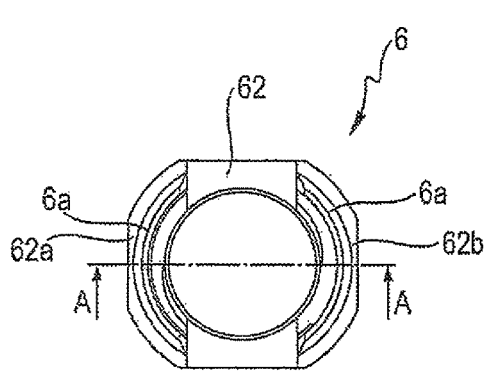
FIG. 7 shows a top view of the receiving part shown in FIGS. 5 and 6.
Figure 8:
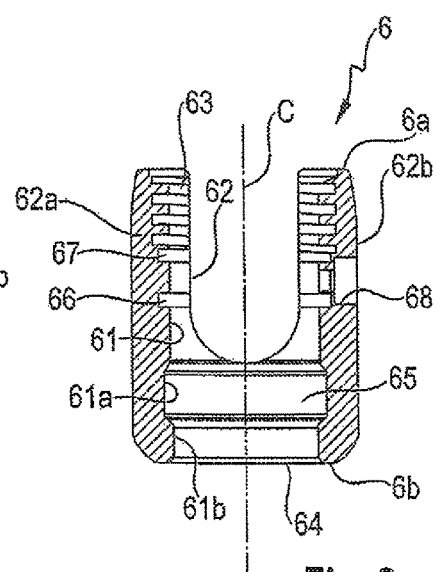
FIG. 8 shows a cross-sectional view of the receiving part shown in FIGS. 5 to 7 along line A-A in FIG. 7.
Figure 9:
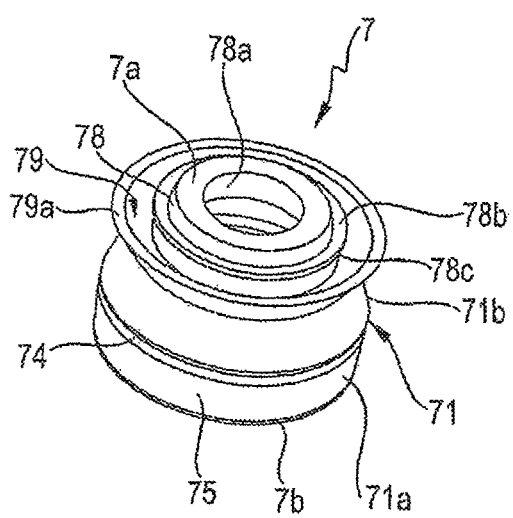
FIG. 9 shows a perspective view from above of a pressure element according to the first embodiment.
Figure 10:
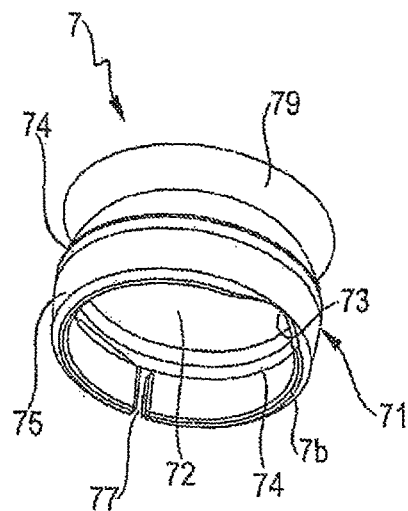
FIG. 10 shows a perspective view from the bottom of the pressure element shown in FIG. 9.
Figure 11:
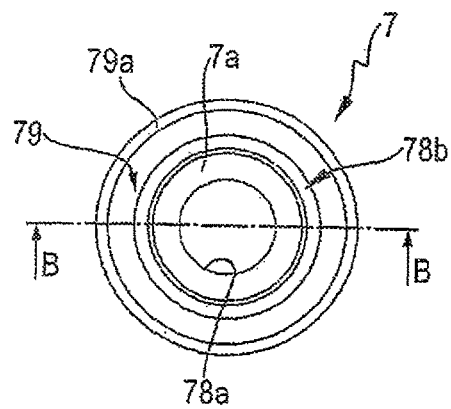
FIG. 11 shows a top view of the pressure element shown in FIGS. 9 and 10.
Figure 12:
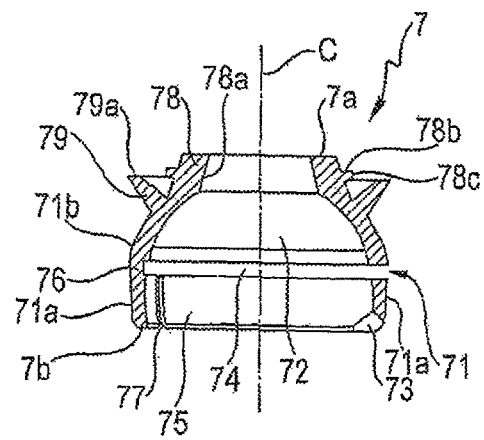
FIG. 12 shows a cross-sectional view of the pressure element of FIGS. 9 to 11 along line B-B in FIG. 11.
Figure 16:
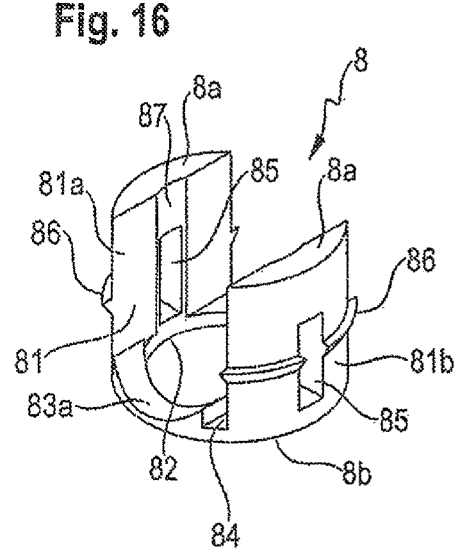
FIG. 16 shows a perspective view from above of a rod receiving element according to the first embodiment.
Figure 17:
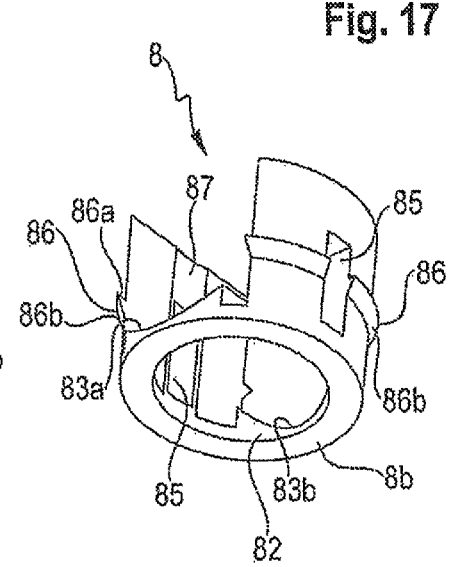
FIG. 17 shows a perspective view from the bottom of the rod receiving element of FIG. 16.
Figure 18:
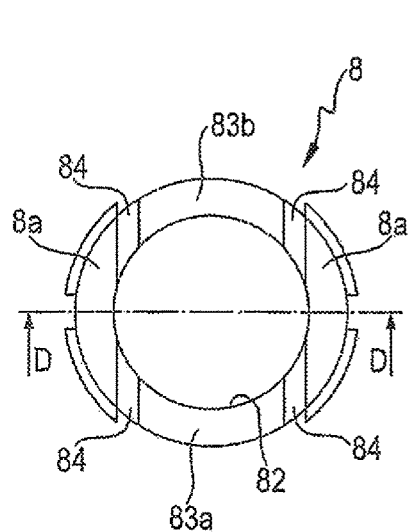
FIG. 18 shows a top view of the rod receiving element shown in FIGS. 16 and 17.
Figure 19:
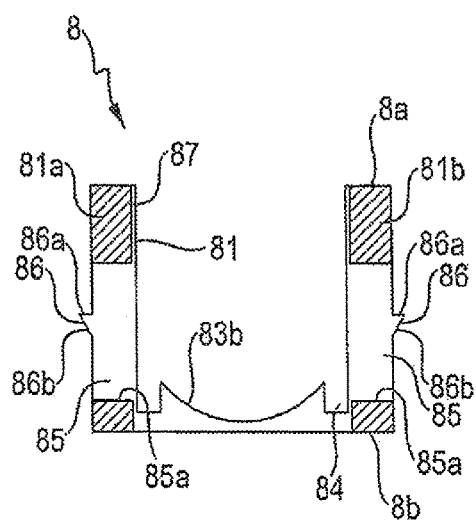
FIG. 19 shows a cross-sectional view of the rod receiving element of FIGS. 16 to 18 along line D-D in FIG. 18.

In the locked condition, as shown in FIGS. 3 and 4, the anchoring element 1 may assume a greater pivot angle relative to the receiving part 6 when the anchoring element 1 is abutting the recessed portion 73 of the pressure element 7 with the shank 2, than when the anchoring element 1 is pivoted in an opposite or other directions.

If the position of the rod 100 relative to the receiving part 6 has to be corrected or adjusted, the locking element 10 can be rotated backwards until the pressure on the rod 100 is relieved and the rod 100 becomes freely movable again. Because the slit ring 75 is held in the narrowing portion 61b of the receiving part 6, the locking of the head 3 is maintained.

Figure 27:
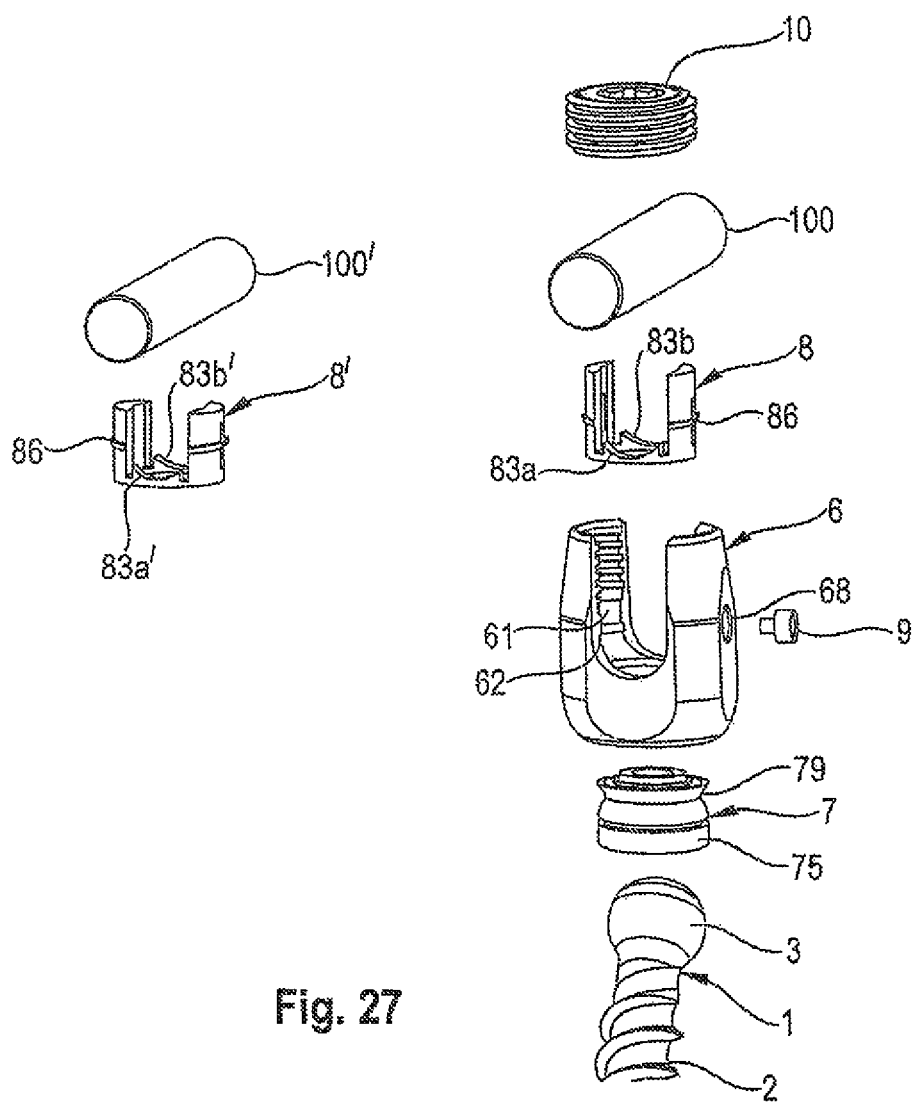
FIG. 27 shows a perspective exploded view of a kit of a coupling assembly with different rod receiving elements for accommodating rods with different diameters.

FIG. 27 shows a kit of a bone anchoring device with a coupling assembly comprising at least two rod receiving elements 8, 8'. The coupling assembly 5 including the receiving part 6, the pressure element 7, and the rod receiving element 8 is the same as previously described and can have all the features and modifications as previously described. The rod receiving element 8 is a first rod receiving element and is sized and configured to receive the rod 100 that is a first rod having a first outer diameter. The rod receiving element 8' is a second rod receiving element that is sized and configured to receive a second rod 100' that has a second diameter smaller than the first diameter of the first rod 100. Consequently, rod support surfaces 83a', 83b' of the second rod receiving element 8' may have a smaller curvature that corresponds to the second rod 100' having the second diameter. Furthermore, a height of the upstanding legs 81a', 81b' of the second rod receiving element 8' is smaller than a height of the legs 81a, 81b of the first rod receiving element 8, so as to project only slightly over the upper rod surface of the second rod 100' when the second rod 100' is inserted into the rod receiving element 8'. An outer diameter of the rod receiving element 8' and an inner diameter, for example, of the opening 82, may be the same as for the first rod receiving element 8.

FIG. 28 shows the bone anchoring device which has the second rod receiving element 8' and which is coupled to the second rod 100'. FIG. 29 shows the first bone anchoring device which has the first rod receiving element 8 and is coupled to the first rod 100 for comparison. Because the height of the second rod receiving element 8' is smaller than the height of the first rod receiving element 8, the locking element 10 must be screwed deeper in between the legs 62a, 62b of the receiving part 6, as depicted in FIG. 28, as compared to the case in which the first diameter rod 100 and the first rod receiving element 8 are used, as depicted in FIG. 29.

By means of the kit, with a single bone anchoring device kit, various rods with various diameters can be used by selecting the appropriate rod receiving element. It is even possible to use a rod with sections having different diameters, for example, a rod that has a first diameter in one section and a second diameter smaller than the first diameter in another section. In this case, a first bone anchoring device may be paired with a first rod receiving element with a greater height, and a second bone anchoring device may be paired with a second rod receiving element with a smaller height. The kit opens the use of the device to a variety of different applications, and provides the advantage of a modular system. For example, for the bone anchoring element, all kinds of anchoring elements can be used and combined with the coupling assembly. These anchoring elements may be, for example, e.g. screws of different lengths, with different diameters, cannulated screws, screws with different thread forms, nails, hooks, etc. The head and the shank of some screws may also be separate parts that are connectable to each other.

Additionally, a kit of the coupling assembly with at least one further pressure element can be provided. The additional or alternative pressure element or elements can be designed without a recess for an enlarged pivot angle or can have several recesses, for example, two or more equidistantly spaced recesses for having enlarged pivot angles in two or more directions. By combining the different elements from the pressure element and the rod receiving element with a receiver, the most suitable bone anchoring device for a specific clinical application can be easily generated or selected.

Figure 30:
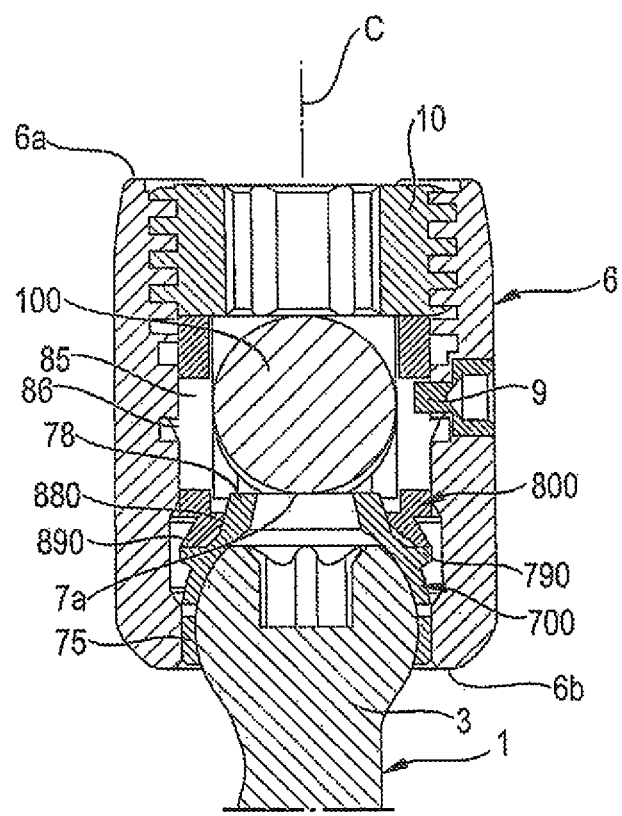
FIG. 30 shows a cross-sectional view of a bone anchoring device according to a second embodiment with inserted rod and locking element, wherein the section is taken in a plane containing the central axis of the coupling assembly and that is perpendicular to the rod axis.

A second embodiment of the coupling assembly is described with reference to FIG. 30. FIG. 30 shows the bone anchoring device with the anchoring element 1, the rod 100 and the locking element 10 as in the previous embodiments. The pressure element 700 differs from the pressure element of the previous embodiments in that the pressure element 700 does not have a deformable portion that cooperates with the rod receiving element 800 or an annular projection for connecting it in an interference-fit manner to the rod receiving element 800. Instead of this, the pressure element 700 has a non-deformable annular projection 790 with a flat upper surface that cooperates with a collar-like conically widening projection 890 at a second end of the rod receiving element 800. The collar like projection 890 is similar to but has a substantially inverse shape compared to the collar 79 described in previous embodiments. The projection 890 is slightly flexible and engages the flat upper surface of the projection 790 of the pressure element 700 when a load acts onto the rod receiving element 800 via the locking element 10. Furthermore, the rod receiving element 800 also has at the second end an inner projection 880 with a conical inner surface that is configured to engage a conical outer surface of a conical portion of the pressure element 700 in order to temporarily hold the pressure element 700. In this embodiment, deformation takes place at the rod receiving element 800. The effect is the same as in the previously described embodiments, namely that the rod receiving element 800 can move slightly downward when the locking element 10 is tightened, so that the first end surface 7a of the pressure element 700 moves upward to contact the rod 100 and the locking element 10 can engage the rod 100.

Various modifications of the embodiments described above may also be contemplated or implemented. For example, the receiving part is not limited to the exact shape as shown. The recess for the rod does not have to have an exact U-shape. In addition, the bore can have several sections with different widths, as long as the enlarged portion that provides space for expansion of the pressure element is provided. The narrowing portion at the bottom of the receiving part is shown to be tapered, but can also be rounded. Also, for example, the external surface of the cap-like portion at the bottom end of the pressure element can be rounded. Combinations of the respective surfaces of the receiving part and the pressure element that cooperate to clamp the head can be tapered and tapered, tapered and rounded or vice-versa, or rounded and rounded, etc. The pressure element may, for example, have a cylindrical portion instead of the conical portion 78.

The head, and correspondingly the interior chamber and/or the exterior surface of the cap-like portion of the pressure element can have various other shapes. For example, two opposite flattened portions may be present that make the connection between the head and the receiving part a monoplanar connection.

Furthermore, all different kinds of rods can be used. While rods with a smooth surface are shown, roughened rods or rods having various other structures, for example, may be used. The rods may also be flexible rods.

While a number of different embodiments are disclosed herein, it should also be appreciated and understood that different components from the different embodiments can be mixed and matched to produce a variety of still more different embodiments.

While the present invention has been described in connection with certain exemplary embodiments, it is to be understood that the invention is not limited to the disclosed embodiments, but is instead intended to cover various modifications and equivalent arrangements included within the spirit and scope of the appended claims, and equivalents thereof.

What is claimed is:

1. A coupling assembly for coupling a rod to a bone anchoring element, the coupling assembly comprising:
a receiving part having a first end, a second end, and a central axis extending though the first end and the second end, wherein the receiving part defines a recess at the first end for receiving the rod, and an accommodation space for accommodating a head of the bone anchoring element, the accommodation space having an opening at the second end for inserting the head;
a pressure element having a first end and a second end, and comprising a non-compressible portion at the first end of the pressure element and a compressible portion that defines at least part of a chamber open to the second end of the pressure element, wherein at least one slit is defined by a wall of the compressible portion and is located entirely in the compressible portion to render the chamber compressible for inserting and clamping the head, the pressure element further comprising a first engagement portion positioned away from the compressible portion; and
a rod receiving element that is a separate piece from and movable relative to the pressure element, the rod receiving element having a first end, a second end, and a channel open to the first end of the rod receiving element for receiving the rod, and comprising a second engagement portion;
wherein when the pressure element is positioned at least partially in the accommodation space with the chamber opening towards the second end of the receiving part and the rod receiving element is positioned in the receiving part with the channel opening towards the first end of the receiving part and with the second engagement portion engaging the first engagement portion, at least part of the rod receiving element surrounds at least part of the pressure element in a radial direction, while one of the first or second engagement portions is deformable by the other one of the first or second engagement portions for moving the pressure element and the rod receiving element axially relative to one another while a width of the non-compressible portion at the first end of the pressure element taken in a direction perpendicular to the central axis remains constant.

2. The coupling assembly of claim 1, wherein the receiving part comprises a narrowing portion at an inner wall near the opening that is configured to cooperate with an external surface of the compressible portion of the pressure element to clamp an inserted head in the pressure element and to prevent removal of the head through the opening.

3. The coupling assembly of claim 2, wherein the narrowing portion of the receiving part and the external surface of the compressible portion of the pressure element is each tapered or rounded.

4. The coupling assembly of claim 1, wherein the pressure element is configured to be rotatable in the receiving part.

5. The coupling assembly of claim 1, wherein the at least one slit of the pressure element has a first portion spaced apart from the second end of the pressure element that extends circumferentially at least partially around a central axis of the pressure element, and a second portion that extends from the second end of the pressure element to the first portion, and wherein the first portion extends circumferentially away from the second portion and is longer than the second portion.

6. The coupling assembly of claim 5, wherein the first portion defines a slit ring that is configured to laterally encompass an inserted head.

7. The coupling assembly of claim 1, wherein the compressible portion of the pressure element has a recessed portion at the second end that is configured to permit the bone anchoring element to pivot relative to the coupling assembly at a larger pivot angle in the direction of the recessed portion than in other radial directions.

8. The coupling assembly of claim 1, wherein the non-compressible portion of the pressure element comprises a substantially cone-segment shaped or cylindrical and a coaxial conical or cylindrical bore extending from the first end the first end of the pressure element to the chamber.

9. The coupling assembly of claim 1, wherein the first engagement portion of the pressure element comprises a projection that extends in a radial direction beyond an outer circumference of the first end of the pressure element.

10. The coupling assembly of claim 9, wherein the projection is a substantially conically-shaped collar that extends in a direction away from an outer surface of the pressure element and towards the first end of the pressure element.

11. The coupling assembly of claim 1, wherein the rod receiving element comprises two legs and a base connecting the two legs to define the channel for receiving the rod.

12. The coupling assembly of claim 1, wherein the receiving part or the rod receiving element comprises a projection configured to engage a second recess on the other one of the receiving part or the rod receiving element to form a stop for holding the rod receiving element in the receiving part at an insertion position to facilitate insertion of the head of the bone anchoring element into the pressure element.

13. The coupling assembly of claim 1, wherein the rod receiving element or the receiving part comprises a projection configured to engage a second recess on the other one of the receiving part or the rod receiving element to form a stop for holding the rod receiving element in the receiving part at a position where the receiving part blocks removal of an inserted head from the pressure element.

14. The coupling assembly of claim 1, wherein the pressure element is configured to be arranged in the receiving part between the rod receiving element and the second end of the receiving part, and is configured to be held at an insertion position for inserting the head of the bone anchoring element.

15. A kit comprising the coupling assembly of claim 1, wherein the rod receiving element is a first rod receiving element having a channel with a first depth configured to receive a first rod with a first rod diameter, and wherein the kit further comprises a second rod receiving element that has a channel with a second depth different than the first depth and configured to receive a second rod with a second rod diameter.

16. A bone anchoring device comprising:
a bone anchoring element having a shank for anchoring to a bone and a head; and
a coupling element for coupling a rod to the bone anchoring element, the coupling element comprising:
a receiving part having a first end, a second end, and a central axis extending though the first end and the second end, wherein the receiving part defines a recess at the first end for receiving the rod, and an accommodation space for accommodating the head of the bone anchoring element, the accommodation space having an opening at the second end for inserting the head; and
a pressure element having a first end and a second end, and comprising a non-compressible portion at the first end of the pressure element and a compressible portion that defines at least part of a chamber open to the second end of the pressure element, wherein at least one slit is defined by a wall of the compressible portion and is located entirely in the compressible portion to render the chamber compressible for inserting and clamping the head, the pressure element further comprising a first engagement portion positioned away from the compressible portion; and
a rod receiving element that is a separate piece from and movable relative to the pressure element, the rod receiving element having a first end, a second end, and a channel open to the first end of the rod receiving element for receiving the rod, and comprising a second engagement portion;
wherein when the pressure element is positioned at least partially in the accommodation space with the chamber opening towards the second end of the receiving part and the rod receiving element is positioned in the receiving part with the channel opening towards the first end of the receiving part and with the second engagement portion engaging the first engagement portion, at least part of the rod receiving element surrounds at least part of the pressure element in a radial direction, while one of the first or second engagement portions is deformable by the other one of the first or second engagement portions for moving the pressure element and the rod receiving element axially relative to one another while a width of the non-compressible portion at the first end of the pressure element taken in a direction perpendicular to the central axis remains constant.

17. The bone anchoring device of claim 16, further comprising:
a locking element movable axially in the receiving part for locking the head and the rod relative to the receiving part; and
the rod;
wherein when the rod is in the channel of the rod receiving element, the locking element is configured to contact the first end of the rod receiving element to move the rod receiving element axially relative to the pressure element.

18. A method of coupling a rod to a bone via a bone anchoring device, the bone anchoring device comprising a bone anchoring element having a shank and a head, and a coupling assembly comprising a receiving part having a first end, a second end, and a central axis extending though the first end and the second end, wherein the receiving part defines a recess at the first end for receiving the rod, and an accommodation space for accommodating the head of the bone anchoring element, the accommodation space having an opening at the second end for inserting the head, a pressure element having a first end and a second end, and comprising a non-compressible portion at the first end of the pressure element and a compressible portion that defines at least part of a chamber open to the second end of the pressure element, wherein at least one slit is defined by a wall of the compressible portion and is located entirely in the compressible portion to render the chamber compressible for inserting and clamping the head, the pressure element further comprising a first engagement portion positioned away from the compressible portion, a rod receiving element that is a separate piece from and movable relative to the pressure element, the rod receiving element having a first end, a second end, and a channel open to the first end of the rod receiving element for receiving the rod, and comprising a second engagement portion, and a locking element, the method comprising:
inserting a shank of the bone anchoring element into a bone;
adjusting an angular position of the receiving part relative to the bone anchoring element when the head is held in the compressible portion of the pressure element, the pressure element is positioned at least partially in the accommodation space with the chamber opening towards the second end of the receiving part and the rod receiving element is positioned in the receiving part with the channel opening towards the first end of the receiving part;
inserting the rod into the recess of the receiving part and the channel of the rod receiving element;
advancing the locking element in the receiving part to a first position wherein at least part of the rod receiving element surrounds at least part of the pressure element in a radial direction, the locking element exerts pressure on the rod receiving element and the rod receiving element exerts pressure on the pressure element via engagement of the second engagement portion with the first engagement portion to clamp the head, and the first and second engagement portions are unbiased; and
further advancing the locking element in the receiving part to a second position wherein at least part of the rod receiving element surrounds at least part of the pressure element in the radial direction, and wherein one of the first or second engagement portions is deformed by the other one of the first or second engagement portions to move the rod receiving element axially relative to the pressure element for clamping the rod relative to the coupling assembly while a width of the non-compressible portion at the first end of the pressure element taken in a direction perpendicular to the central axis remains constant.

19. The method of claim 18, further comprising inserting the head through the opening of the receiving part prior to inserting the shank of the bone anchoring element into the bone to connect the coupling assembly with the bone anchoring element.

20. The method of claim 18, further comprising inserting the head through the opening of the receiving part after inserting the shank of the bone anchoring element into the bone to connect the coupling assembly with the bone anchoring element.

* * * * *

UNITED STATES PATENT AND TRADEMARK OFFICE
CERTIFICATE OF CORRECTION

| | | |
|---|---|---|
| PATENT NO. | : 10,022,158 B2 | Page 1 of 1 |
| APPLICATION NO. | : 15/229740 | |
| DATED | : July 17, 2018 | |
| INVENTOR(S) | : Lutz Biedermann et al. | |

It is certified that error appears in the above-identified patent and that said Letters Patent is hereby corrected as shown below:

On the Title Page
Column 1, item (54), Title, Line 3    After "assembly" insert -- with --

Column 1, item (54), Title, Line 4    Delete "elements" and insert -- elements, --

In the Specification
Column 1, Line 3    After "assembly" insert -- with --

Column 1, Line 4    Delete "elements" and insert -- elements, --

In the Claims
Column 14, Line 29, Claim 8    After "cylindrical" insert -- portion --

Column 14, Lines 30-31, Claim 8    After "the first end" delete "the first end"

Signed and Sealed this
Seventh Day of July, 2020

Andrei Iancu
*Director of the United States Patent and Trademark Office*